(12) United States Patent
Liu

(10) Patent No.: US 12,306,156 B2
(45) Date of Patent: May 20, 2025

(54) TERMINAL DEVICE

(71) Applicant: Rayprus Technology (Foshan) Co., Ltd., Foshan (CN)

(72) Inventor: Jian-Zong Liu, New Taipei (TW)

(73) Assignee: Rayprus Technology (Foshan) Co., Ltd., Foshan (CN)

( * ) Notice: Subject to any disclaimer, the term of this patent is extended or adjusted under 35 U.S.C. 154(b) by 123 days.

(21) Appl. No.: 18/216,743

(22) Filed: Jun. 30, 2023

(65) Prior Publication Data

US 2024/0329020 A1    Oct. 3, 2024

(30) Foreign Application Priority Data

Mar. 29, 2023  (CN) .......................... 202310324219.6

(51) Int. Cl.
| | |
|---|---|
| *G01N 33/00* | (2006.01) |
| *G01D 11/24* | (2006.01) |
| *G01D 11/30* | (2006.01) |
| *G01N 5/02* | (2006.01) |
| *G06F 1/16* | (2006.01) |
| *H04M 1/02* | (2006.01) |

(52) U.S. Cl.
CPC ....... *G01N 33/0009* (2013.01); *G01D 11/245* (2013.01); *G01D 11/30* (2013.01); *G01N 5/02* (2013.01); *G06F 1/1684* (2013.01); *H04M 1/026* (2013.01)

(58) Field of Classification Search
CPC ......... G01D 11/30; G01D 11/245; G01N 5/02
See application file for complete search history.

(56) References Cited

U.S. PATENT DOCUMENTS 6,085,576 A  *  7/2000  Sunshine ........... G01N 33/0031
                                                    340/634

FOREIGN PATENT DOCUMENTS

| CN | 111049046 A | * | 4/2020 | ............ G01D 11/28 |
| CN | 113219131 A | * | 8/2021 | ......... G01N 33/0009 |
| CN | 214503565 U | * | 10/2021 | |
| CN | 218470472 U | * | 2/2023 | |
| KR | 100793918 B1 | * | 1/2008 | |
| WO | WO-2020184721 A1 | * | 9/2020 | ............ G01N 27/12 |
| WO | WO-2021031712 A1 | * | 2/2021 | |

* cited by examiner

*Primary Examiner* — Jamel E Williams
(74) *Attorney, Agent, or Firm* — ScienBiziP, P.C.

(57) ABSTRACT

A terminal device includes a body, a smell sensor, a housing, an elastic piece, and a coil. A groove is defined on the body, the groove has a bottom wall. The smell sensor is fixed to the bottom wall. The housing covers the groove. The elastic piece includes a fixing area and a deformable area disposed around the fixing area. The fixing area is fixed to the housing, the deformable area can be deformed relative to the fixing area. The coil can generate a magnetic field to deform the deformable area toward the bottom wall, causing the deformable area and the bottom wall to cooperatively form an accommodating cavity, the smell sensor can be accommodated in the accommodating cavity.

9 Claims, 6 Drawing Sheets

TERMINAL DEVICE

FIELD

The subject matter herein generally relates to smell detection, and more particularly, to a terminal device with a smell detection function.

BACKGROUND

Smell sensors can detect the smell of gases in the environment. However, the smell sensor may need a long detection time, waiting for the smell molecules being getting uniform and stable in the environment, otherwise the test result of smell sensors is inaccurate. Therefore, there is a room for improvement in the art.

BRIEF DESCRIPTION OF THE DRAWINGS

Implementations of the present technology will now be described, by way of example only, with reference to the attached figures.

DETAILED DESCRIPTION

Figure 1:
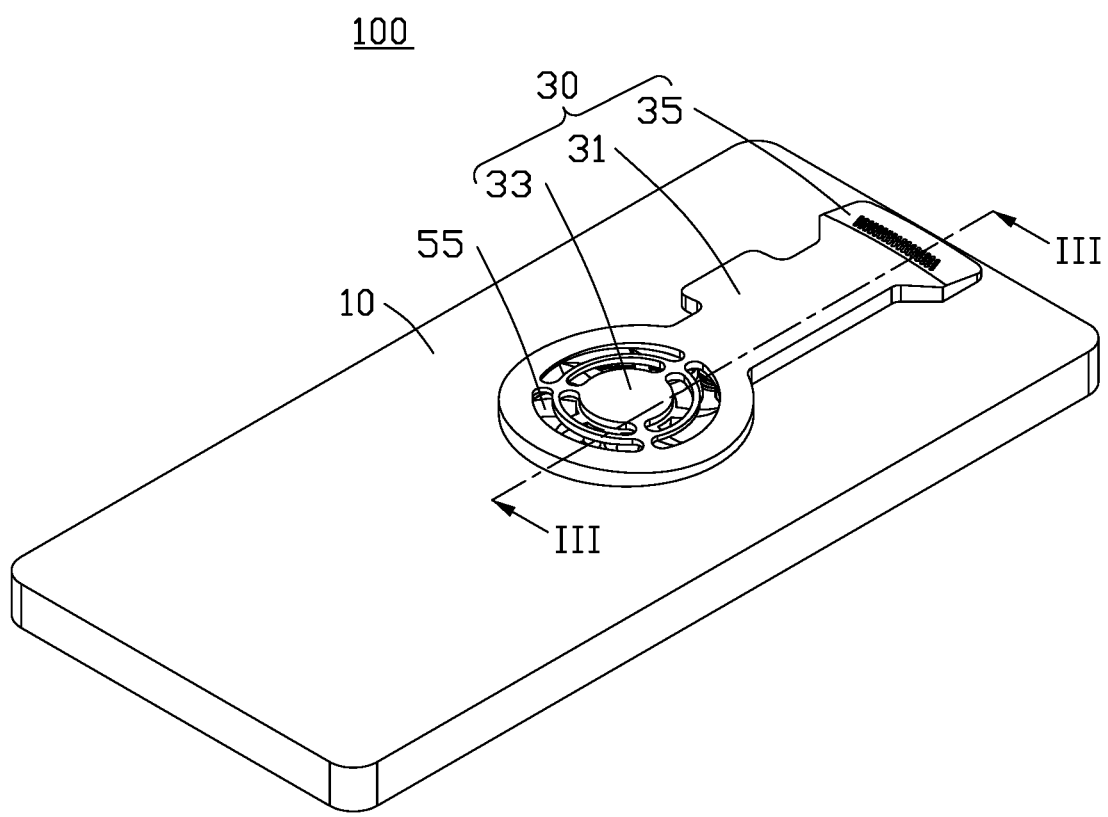
FIG. 1 is a diagrammatic view of an embodiment of a terminal device according to the present disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale, and the proportions of certain parts may be exaggerated to better illustrate details and features of the present disclosure.

The term "comprising," when utilized, means "including, but not necessarily limited to"; it specifically indicates open-ended inclusion or membership in the so-described combination, group, series, and the like.

Some embodiments of the present disclosure will be described in detail with reference to the drawings. If there is no conflict, the following embodiments and features in the embodiments can be combined with each other.

Figure 2:
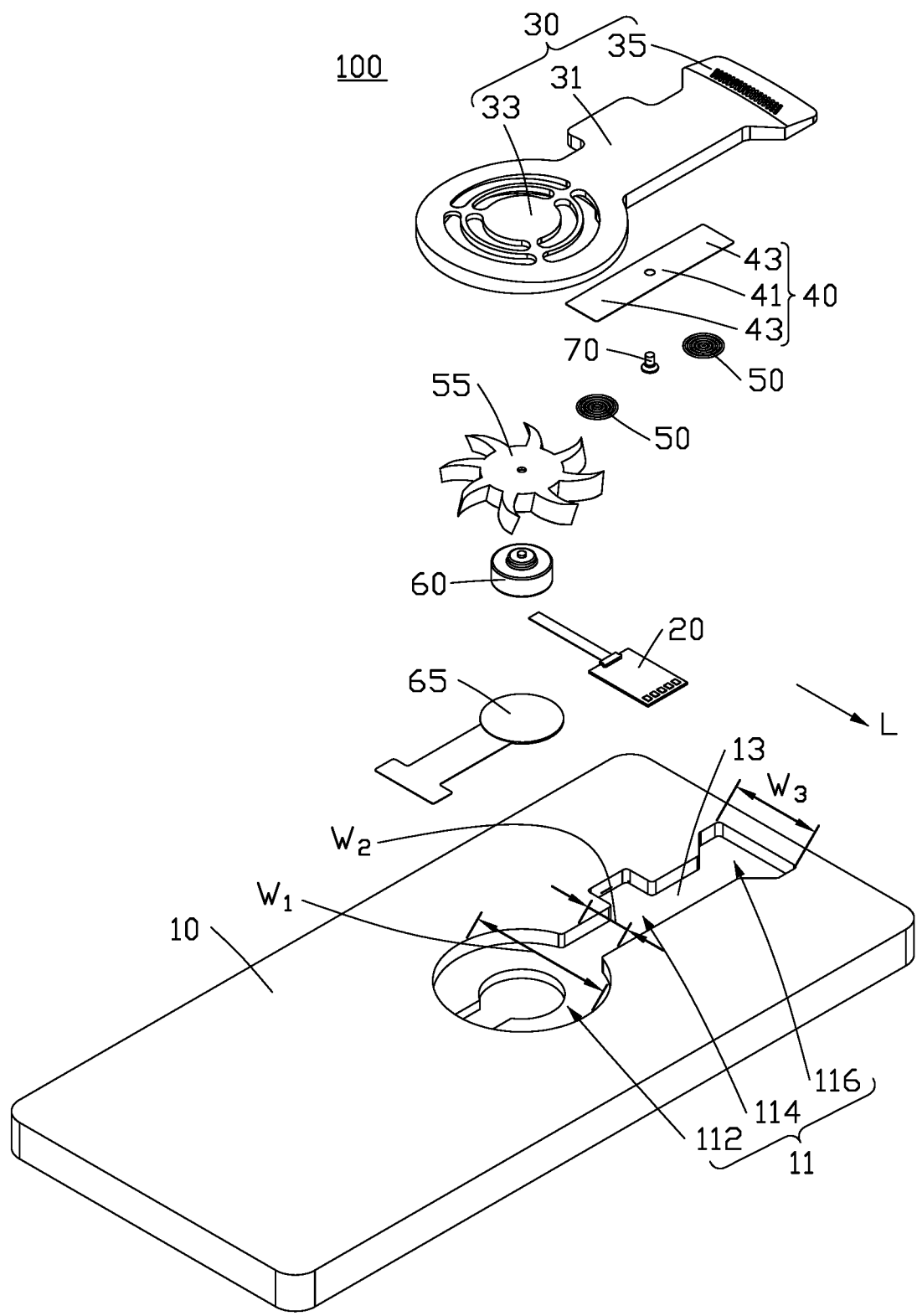
FIG. 2 is an exploded view of the terminal device of FIG. 1.
Figure 3:
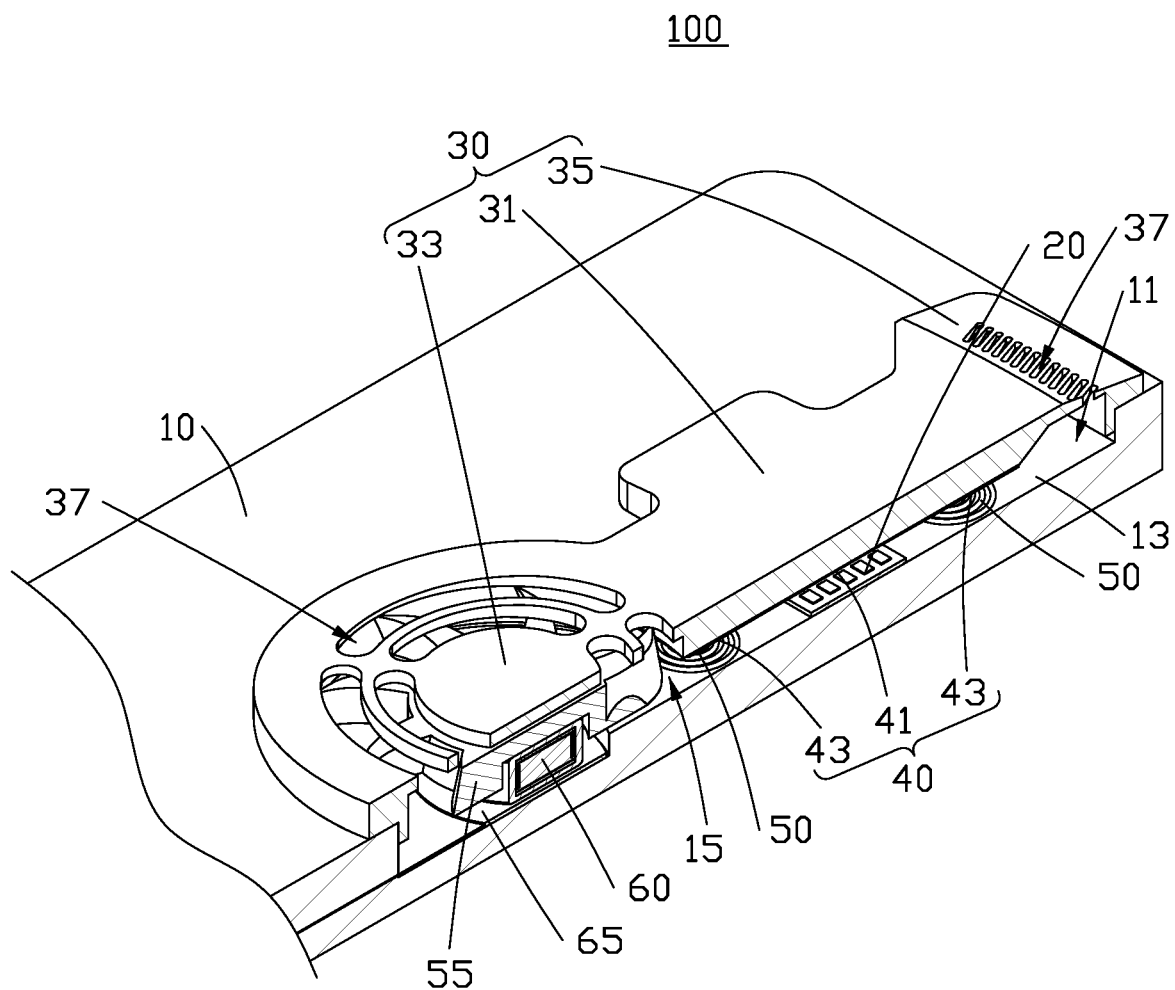
FIG. 3 is a cross-sectional view taken along line III-III of FIG. 1.

Referring to FIGS. 1, 2, and 3, a terminal device 100 is provided according to an embodiment of the present disclosure. The terminal device 100 includes a smell sensor 20 having a smell detection function. Smell molecules 85 in the air can be absorbed and adhered on the smell sensor 20, causing a mass change of the smell sensor 20. The smell sensor 20 can further determine a type and smell of the smell molecules 85 according to the mass change. The terminal device 100 can be a portable device, such as a mobile phone, a wearable device, etc. The terminal device 100 can also be a larger device, such as a refrigerator. In the embodiment, the terminal device 100 is a mobile phone.

The terminal device 100 further includes a body 10, a housing 30, an elastic piece 40, and a coil 50. The coil 50 can generate a magnetic field to deform the elastic piece 40. When the elastic piece 40 deforms, the elastic piece 40 and the body 10 cooperatively form an accommodating cavity 80 (shown in FIG. 5). The smell sensor 20 is accommodated in the accommodating cavity 80. The smell molecules 85 are also limited in the accommodating cavity 80. The smaller the accommodating cavity 80, the more stable the smell molecules 85 adhered on the smell sensor 20, and the faster the response speed of the smell sensor 20, to improve detection accuracy of the smell sensor 20.

A groove 11 is defined on the body 10. The groove 11 has a bottom wall 13. The groove 11 includes a first area 112, a second area 114, and a third area 116. The second area 114 communicates with the first area 112 and the third area 116. The smell sensor 20 is fixed to the bottom wall 13 of the second area 114.

The housing 30 is detachably connected to the body 10, and the housing 30 can cover the groove 11. A portion of the housing 30 is accommodated in the groove 11, and another portion of the housing 30 protrudes from the body 10, so that the housing 30 and the body 10 cooperatively form a space 15. The smell sensor 20, the elastic piece 40, and the coil 50 are accommodated in the space 15.

The housing 30 includes a sealing area 31, a first hollow area 33, and a second hollow area 35. The first hollow area 33 and the second hollow area 35 are disposed on two sides of the sealing area 31 respectively. At least one through hole 37 is defined on both the first hollow area 33 and the second hollow area 35 to facilitate gas exchange between the interior and exterior of the terminal device 100. The first hollow area 33 is engaged with a shape of the first area 112 and disposed correspondingly. The sealing area 31 matches the second area 114 in shape, and the sealing area 31 and the second area 114 correspond to each other. The second hollow area 35 matches the third area 116 in shape, and the second hollow area 35 and the third area 116 correspond to each other. The first hollow area 33 can be used as an air inlet, and the second hollow area 35 can be used as an air outlet, so as to realize gas exchange between the interior and exterior of the terminal device 100.

A projection of the sealing area 31 on the body 10 covers a projection of the elastic piece 40 on the body 10. The elastic piece 40 includes a fixing area 41 and a deformable area 43 disposed around the fixing area 41. In the embodiment, the elastic piece 40 is substantially rectangular. Two deformable areas 43 are disposed at both ends of the fixing area 41. One of the deformable areas 43 is disposed toward the first area 112, and the other of the deformable areas 43 is disposed toward the third area 116. The fixing area 41 is spaced apart from the smell sensor 20. In other embodiments, the deformable area 43 can be disposed on the circumference of the fixing area 41. The fixing area 41 is fixed to the sealing area 31, and the deformable area 43 can be deformed relative to the fixing area 41. In the embodiment, the elastic piece 40 is fixed to the fixing area 41 by a fixing member 70 (such as a screw).

Figure 4:
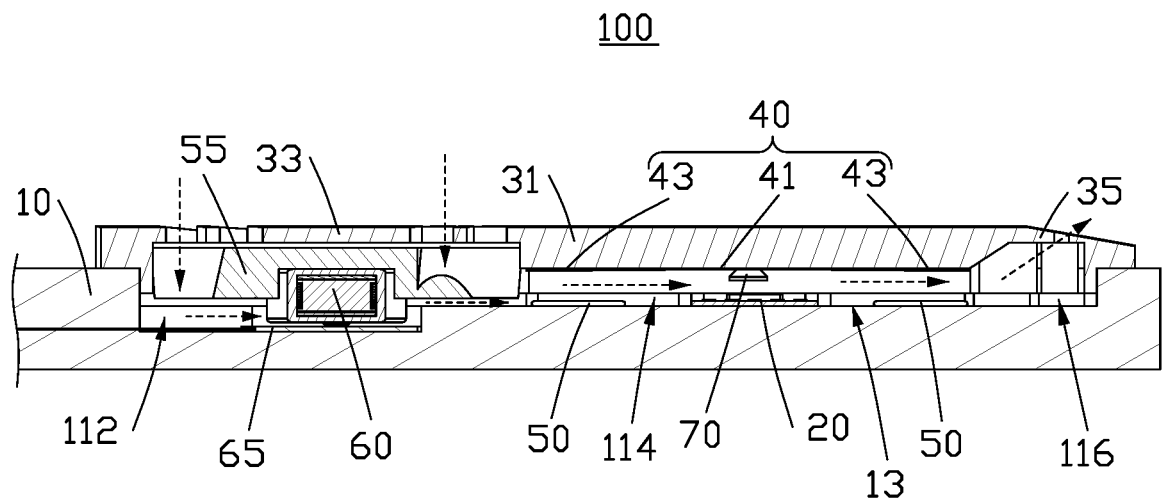
FIG. 4 is a cross-sectional view of the terminal device before an elastic piece of the terminal device is deformed.
Figure 5:
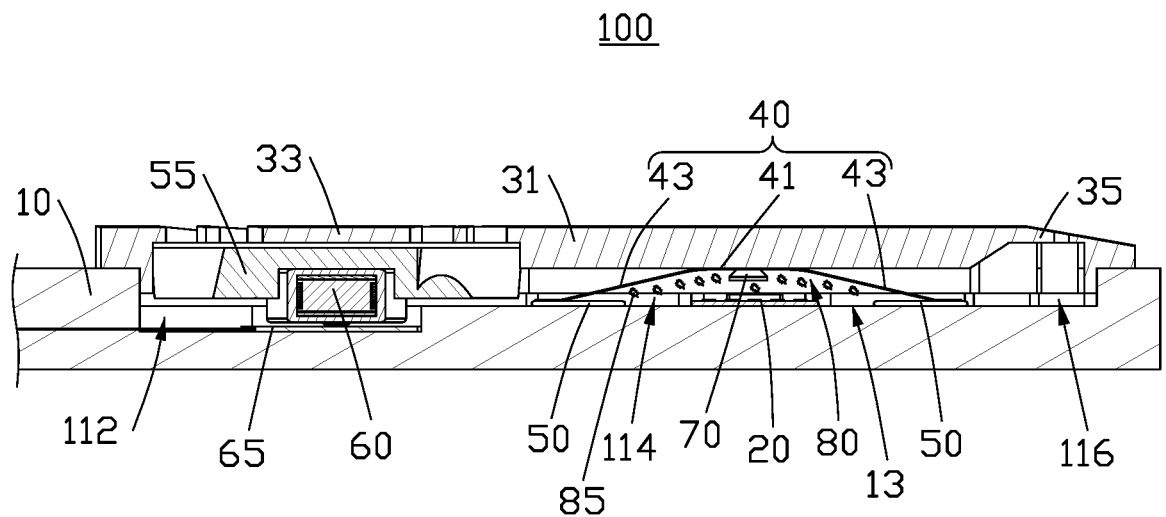
FIG. 5 is a cross-sectional view of the terminal device showing the elastic piece is deformed.

Referring to FIGS. 4 and 5, in some embodiments, the elastic piece 40 itself is not magnetic but can be attracted by the magnetic field. For example, the elastic piece 40 is made of a material such as iron, cobalt, and nickel. The coil 50 can be fixed to the bottom wall 13, and the coil 50 can generate a magnetic force for attracting the deformable areas 43, so that the deformable areas 43 bent toward the bottom wall 13. The deformed elastic piece 40 and the bottom wall 13 in the second area 114 form the accommodating cavity 80, and the smell sensor 20 is accommodated in the accommodating cavity 80, so as to detect the smell molecules 85 in the gas in the accommodating cavity 80.

In other embodiments, the elastic piece 40 is magnetic. That is, the elastic piece 40 can generate a magnetic field. The coil 50 can be fixed to the bottom wall 13, and the coil 50 can generate a magnetic field, which has a direction opposite to that of the magnetic field generated by the elastic piece 40, to attract the deformable areas 43, so that the deformable areas 43 bent toward the bottom wall 13. The deformed elastic piece 40 and the bottom wall 13 in the second area 114 form the accommodating cavity 80, and the smell sensor 20 is accommodated in the accommodating cavity 80, so as to detect the smell molecules 85 in the gas in the accommodating cavity 80.

Figure 6:
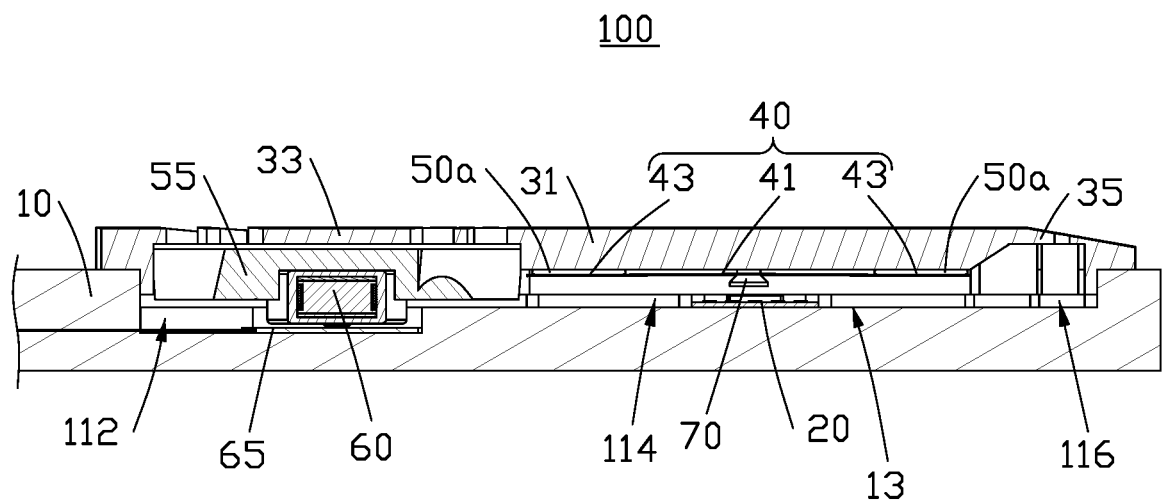
FIG. 6 is a cross-sectional view of another embodiment of a terminal device according to the present disclosure.

Referring to FIG. 6, in some embodiments, the elastic piece 40 is magnetic. A coil 50*a* is fixed to the housing 30, and the coil 50*a* can generate a magnetic field, which has a direction the same as that of the magnetic field generated by the elastic piece 40, to repel the deformable areas 43, so that the deformable areas 43 bent toward the bottom wall 13. The deformed elastic piece 40 and the bottom wall 13 in the second area 114 form the accommodating cavity 80, and the smell sensor 20 is accommodated in the accommodating cavity 80, so as to detect the smell molecules 85 in the gas in the accommodating cavity 80.

Referring to FIGS. 2, 3, 4 and 5, the terminal device 100 may further include a fan 55 and a motor 60. Both the motor 60 and the fan 55 are disposed in the first area 112. The fan 55 is sheathed on the motor 60. A center of the motor 60 is fixed relative to the first area 112. The fan 55 is exposed from the first hollow area 33. The motor 60 can drive the fan 55 to rotate so as to drive outside air into the groove 11.

The terminal device 100 further includes a circuit board 65. The circuit board 65 is disposed in the first area 112 of the groove 11. The motor 60, the smell sensor 20, and the coil 50 are electrically connected to the circuit board 65.

Referring to FIG. 4, when the gas needs to be detected, the fan 55 is first turned on, so that the outside gas can enter the interior of the terminal device 100. Referring to FIG. 5, the coil 50 generates a magnetic field to deform the elastic piece 40. The deformed elastic piece 40 and the bottom wall 13 form a relatively airtight accommodating cavity 80, and the smell sensor 20 detects the gas in the accommodating cavity 80.

Referring to FIGS. 2 and 4, along a direction L perpendicular to the gas flow in the groove 11, a width W2 of the second area 114 is smaller than a width W1 of the first area 112, and the width W2 of the second area 114 is smaller than a width W3 of the third area 116. That is, the width W2 of the second area 114 is the narrowest. When the fan 55 is turned on, the velocity of gas flow in the second area 114 is faster than the velocity of gas flow in each of the first area 112 and the third area 116, causing the smell molecules 85 in the second area 114 to be more uniformly dispersed, thereby improving the detection accuracy. In addition, when the elastic piece 40 is deformed, a volume of the accommodating cavity 80 formed by the elastic piece 40 and the bottom wall 13 is relatively small, which can improve the detection accuracy.

In the present disclosure, the deformable elastic piece 40 is controlled by a magnetic field generated by the coil 50, which is high sensitivity. The deformable elastic piece 40 seals the gas in the small accommodating cavity 80, which can speed up the response time of the smell sensor 20 and improve the detection stability and accuracy of the smell sensor 20. The structure used for smell detection of the present disclosure occupies a small space, and is convenient to be applied to a portable terminal device.

It is to be understood, even though information and advantages of the present embodiments have been set forth in the foregoing description, together with details of the structures and functions of the present embodiments, the disclosure is illustrative only; changes may be made in detail, especially in matters of shape, size, and arrangement of parts within the principles of the present embodiments to the full extent indicated by the plain meaning of the terms in which the appended claims are expressed.

What is claimed is:

1. A terminal device, comprising:
a body defining a groove, the groove having a bottom wall;
a smell sensor fixed to the bottom wall;
a housing covering the groove;
an elastic piece comprises a fixing area and a deformable area disposed around the fixing area, the fixing area fixed to the housing, the deformable area configured to be deformed relative to the fixing area; and
a coil configured to generate a magnetic field to deform the deformable area toward the bottom wall, causing the deformable area and the bottom wall to cooperatively form an accommodating cavity, the smell sensor accommodated in the accommodating cavity;
wherein the housing comprises a sealing area, a first hollow area, and a second hollow area, the first hollow area and the second hollow area are disposed on two sides of the sealing area respectively;
the groove further comprises a first area, a second area, and a third area, the second area communicates with the first area and the third area; and
the first hollow area corresponds to the first area, the sealing area corresponds to the second area, and the second hollow area corresponds to the third area.

2. The terminal device of claim 1, wherein a projection of the sealing area on the body covers a projection of the elastic piece on the body; the fixing area is fixed on the sealing area, and the smell sensor is fixed on the bottom wall of the second area.

3. The terminal device of claim 1, further comprising a fan and a motor, wherein the fan is sheathed on the motor, and the fan is exposed from the first hollow area.

4. The terminal device of claim 1, further comprising a circuit board disposed in the first area.

5. The terminal device of claim 1, further comprising a fixing member, wherein the fixing member fixes the fixing area to the sealing area.

6. The terminal device of claim 1, wherein a width of the second area is smaller than a width of the first area, and the width of the second area is smaller than a width of the third area.

7. The terminal device of claim 1, wherein the elastic piece is made of a material which is attracted by the magnetic field, the coil is fixed to the bottom wall; the deformable area is configured to be attracted by the magnetic field generated by the coil and bent toward the bottom wall.

8. The terminal device of claim 1, wherein the elastic piece is magnetic, the coil is fixed to the bottom wall; and a direction of the magnetic field generated by the coil is opposite to a direction of a magnetic field generated by the elastic piece, causing the deformable area to be bent toward the bottom wall.

9. The terminal device of claim 1, wherein the elastic piece is magnetic, the coil is fixed to the housing; and a direction of the magnetic field generated by the coil is same as a direction of a magnetic field generated by the elastic piece, causing the deformable area to be bent toward the bottom wall.

\* \* \* \* \*